(12) United States Patent
Carrillo Rubio (10) Patent No.: US 9,682,358 B2
(45) Date of Patent: Jun. 20, 2017

(54) RESONANCE-BASED MOLECULAR DISSOCIATOR

(71) Applicant: David Homero Carrillo Rubio, Mexico (MX)

(72) Inventor: David Homero Carrillo Rubio, Mexico (MX)

(*) Notice: Subject to any disclaimer, the term of this patent is extended or adjusted under 35 U.S.C. 154(b) by 0 days.

(21) Appl. No.: 14/902,121

(22) PCT Filed: Jul. 1, 2014

(86) PCT No.: PCT/MX2014/000100
§ 371 (c)(1),
(2) Date: Dec. 30, 2015

(87) PCT Pub. No.: WO2015/002524
PCT Pub. Date: Jan. 8, 2015

(65) Prior Publication Data
US 2016/0144334 A1 May 26, 2016

(30) Foreign Application Priority Data

Jul. 1, 2013 (MX) .................. MX/A/2013/007738
Jun. 14, 2014 (VE) ................. 2014-000778

(51) Int. Cl.
*B01J 19/08* (2006.01)
*C02F 1/00* (2006.01)
*A61L 2/00* (2006.01)

(52) U.S. Cl.
CPC ............. *B01J 19/087* (2013.01); *A61L 2/00* (2013.01); *C02F 1/005* (2013.01); *B01J 2219/0803* (2013.01); *C02F 2201/486* (2013.01)

(58) Field of Classification Search
None
See application file for complete search history.

(56) References Cited

U.S. PATENT DOCUMENTS

| 5,326,446 A | 7/1994 | Binger |
| 7,419,603 B2 | 9/2008 | Cho |
| 7,910,006 B2 | 3/2011 | Vallee |
| 2010/0000852 A1 | 1/2010 | Curtin et al. |

FOREIGN PATENT DOCUMENTS

| CA | 2572434 A1 | 1/2005 |
| EP | 2374753 A1 | 10/2011 |
| MX | 241669 | 1/1996 |
| MX | 244030 | 10/2003 |
| WO | WO2005005009 A2 | 1/2005 |
| WO | WO 2010059751 A2 | 5/2010 |
| WO | WO2012030368 A1 | 3/2012 |

OTHER PUBLICATIONS

International Search Report for PCT/MX2014/000100, mailed on Dec. 3, 2014.

*Primary Examiner* — Kishor Mayekar
(74) *Attorney, Agent, or Firm* — Schmeiser, Olsen & Watts, LLP (57) ABSTRACT

A device consisting of antenna units and connected to a signal generator, capable of dissociating or breaking down molecules in solution, suspension or fluids in general, into their constituent elements, in order to recycle said compounds and eliminate contaminants which, if they remain chemically bound, would be dangerous or harmful to human, plant or animal health is provided.

12 Claims, 10 Drawing Sheets

RESONANCE-BASED MOLECULAR DISSOCIATOR

CROSS-REFERENCE TO RELATED APPLICATIONS

This application claims priority to PCT Application No. PCT/MX2014/000100, having a filing date of Jul. 1, 2014, based off of MX/A/2013007738 having a filing date of Jul. 1, 2013 and VE 2014000778, having a filing date of Jun. 14, 2014 the entire contents of which are hereby incorporated by reference.

FIELD OF TECHNOLOGY

The following relates to the field of impurities removal from a compound and more precisely to a molecule dissociator, in a number of steps, by using very low (VLF), low (LF), and medium frequency (MF) spectral patterns on different signal types, such as phased or out-of-phase unitary pulse, sawtooth, square, or sinusoidal functions, which result from combining together two or more of said functions, then inducing the same to an antenna yielding an electromagnetic field and resulting in an induced resonance to the element to be dissociated of the fluid passing through said antennas.

BACKGROUND

Gas dissociators are known, which produce plasma and use antennas and coils to dissociate a gas passing through a chamber, said gas being energized by a high-frequency (VHF, UHF) antenna and/or set of coils; however said devices, although relating to embodiments of the present invention, do not constitute nothing but the relevant state of art.

Also known are devices for water treatment. Among these devices are those described in, for example, U.S. Pat. Nos. 7,910,006, 7,419,603, 5,326,446, etc., which take advantage of electromagnetic properties in order to treat impurities contained in water, which generally are ionized in water and, and thus are affected by an electromagnetic field having suitable properties. Again, this literature is provided as the state-of-the-art in relation to embodiments of the present invention.

The document with publication number WO 2010059751 describes a method and apparatus to produce hydrogen and oxygen from water. Said apparatus comprises a dissociating chamber, a separation apparatus for separating hydrogen ions from oxygen ions and an ionization device. Water can be dissociated within the dissociating chamber with the help of magnetic and/or electromagnetic fields.

In publication document No. WO 2005005009, which is equivalent to Canadian Patent No. 2572434, titled "Dissociation of molecular water into molecular hydrogen", describes, on page 8, in reference to FIG. 1, that the device comprises a radiant energy transfer reactor, including a first portion adapted to receive water molecules, a second portion where the components of the dissociated water molecules may be separated and removed, and a coil, which develop an electromagnetic field when energy is applied thereto.

Mexican Patent No. 244030 refers to a water treatment system where an electric field is used in order to use a cavitation or shock chamber.

Mexican Patent No. 241669, relates to an apparatus for neutralization of biochemical wastes, comprising the following units: a neutralization chamber, refrigeration, a radio frequency generator, a power generator, a gas regulator, etc.

SUMMARY

Embodiments of the present invention relates to a device capable of dissociating or breaking down molecules in solution, suspension, fluids or gases in general, into their constituent elements, in order to recycle said compounds and remove contaminants which, if they remain chemically bound, would be dangerous or harmful to human, plant or animal health.

Through embodiments of the present invention acids, alkalis and carcinogenic substances, for example, which negatively affect the environment to where the same are disposed off, are decomposed into their constituent molecules.

When applying a resonance frequency by means of an oscilloscope in order to break their bonds, all compound molecules can dissociate into the natural elements they are composed of, said bonds being asymmetrical o symmetrical.

Embodiments of the invention consist in a device comprising a set of antenna units which are physically joined together, not necessarily electrically, and which are sealed with neoprene material, in the center of which a conduit is located, through which the fluid to be decomposed is circulated. Joining together the antenna units used forms said conduit.

To each of these antennas a series of wave functions originated from a wave function spectrum generator are induced, where once said generator is connected to the antennas embodiments of the present invention it creates an electromagnetic field deriving into a resonance frequency, which acts on the fluid causing the molecular rupture of the same. Due to the fact that different wave functions are provided on the antennas, antennas generate, in several steps, radiation spectral patterns so as to efficiently affect the fluid to be treated and dissociate the same into its constituent elements only in one device.

BRIEF DESCRIPTION

Some of the embodiments will be described in detail, with reference to the following figures, wherein like designations denote like members, wherein:

FIG. 10 is a cut of the resonance dissociator, where the white squares represent the antennas, and in the interior of which is arranged the induction coil (shown in black) through which the wave function (represented in FIG. 9) flows; the left side shows the fluid being affected by the magnetic field produced as it passes through the antenna joints.

DETAILED DESCRIPTION

Embodiments of the invention refers to a device, which operates with a series of antennas to which different continuous wave functions are provided, each antenna producing an electromagnetic field, with frequency and time variation, which is the technical basis for the dissociation effected by the dissociator of embodiments of the present invention.

Figure 1:
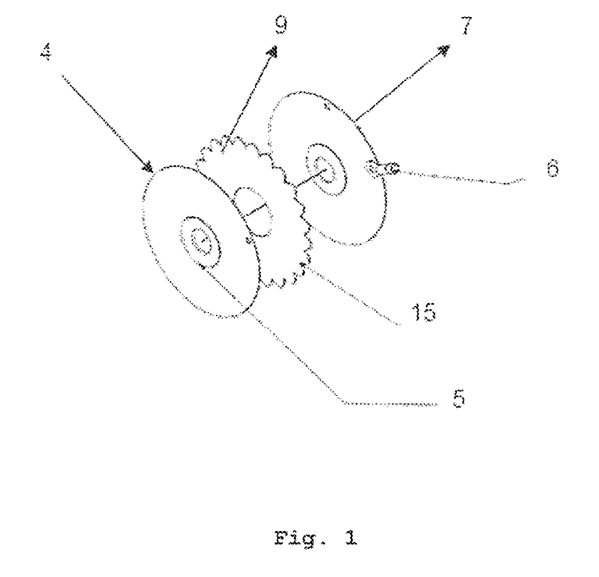
FIG. 1 shows an exploded view of parts of the unitary antenna; wherein (4) is the antenna plate; (6) is the antenna electrical connector; (7) is the antenna plate; (9) is the balanced impedance coil; (5) is the sealing insulator; (15) is the multi-section solenoid; and (16) is a resonance mirror.
Figure 6:
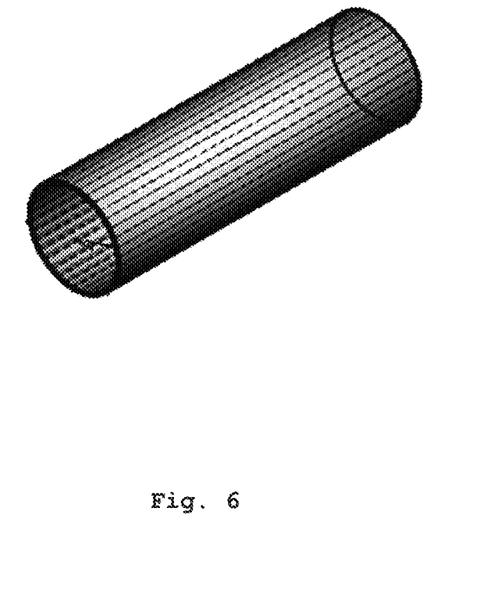
FIG. 6 is a schematic representation of the fluid distribution conduit within the dissociator made of a heat-hardened insulating material.
Figure 8:
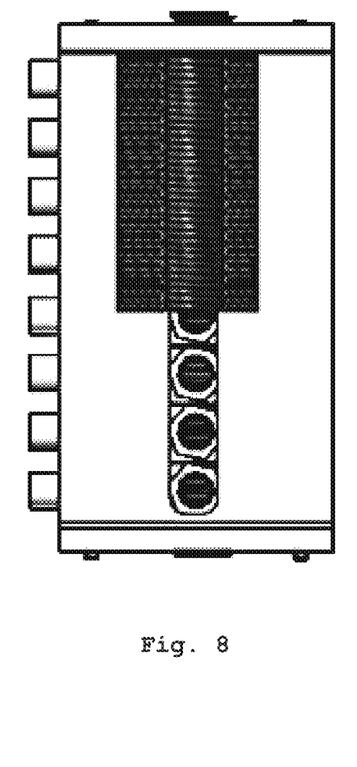
FIG. 8 shows the internal operation of the dissociator and the resultant effect in each step of the molecular dissociation of compounds, and it is also a vertical view of FIG. 7 showing the parts comprised by the device.

Regarding the figures previously described, dissociator (1) comprises an unlimited number of antenna units (FIG. 1) for generating, in a plurality of steps, a spectral pattern radiation of resonance frequency (see FIG. 8). The antenna unit comprises a body or support (2) in which a plurality of concentric antennas are placed (FIG. 1), in the center of which a hollow circular space (11) is located where a conduit (FIG. 6) made of a suitable material is placed for allowing the fluid to be treated to circulate through it.

The dissociated element(s) exit the lateral outlets (10, 12) and the wave function is provided at the connectors (6).

Figure 3:
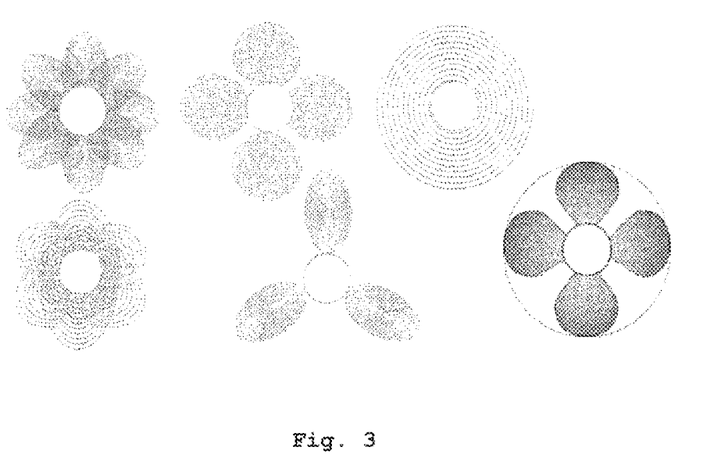
FIG. 3 represents how some shapes of the exemplary windings used by the dissociator can be made.

The dissociator of embodiments of the present invention is built with "n" number of these antenna units (FIG. 1) until the desired pattern is obtained depending on the amount of fluid and element(s) to dissociate, and that said fluid can circulate in the smallest time interval necessary for treatment. Antenna units (FIG. 1) are comprised of two plates (7), separated by a washer (14) between said plates (7), and around the washer (14) a winding is created, like any of those illustrated in FIG. 3, starting and ending on the plastic sheathed electrical eyelet connectors or leads (6) of said units, which can be connected to the same wave function generating source or to individual sources or set of sources, depending on the fluid to be dissociated.

Figure 2:
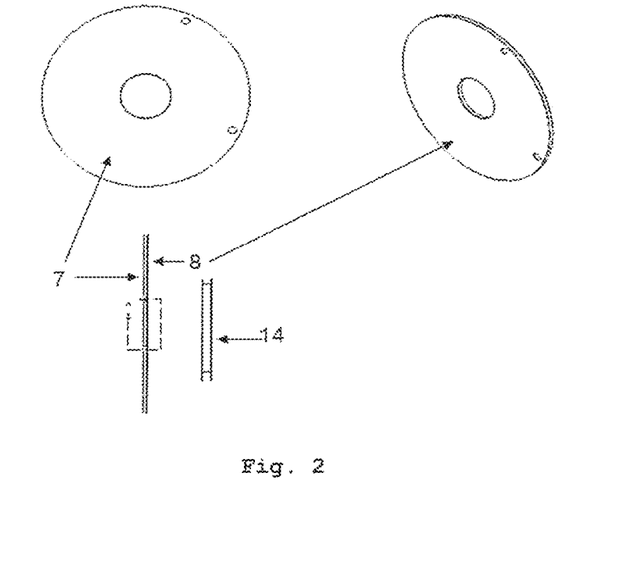
FIG. 2 is an exploded view of parts of the antenna plates; wherein (7) and (8) are conductive plates; and (14) is the washer.
Figure 4:
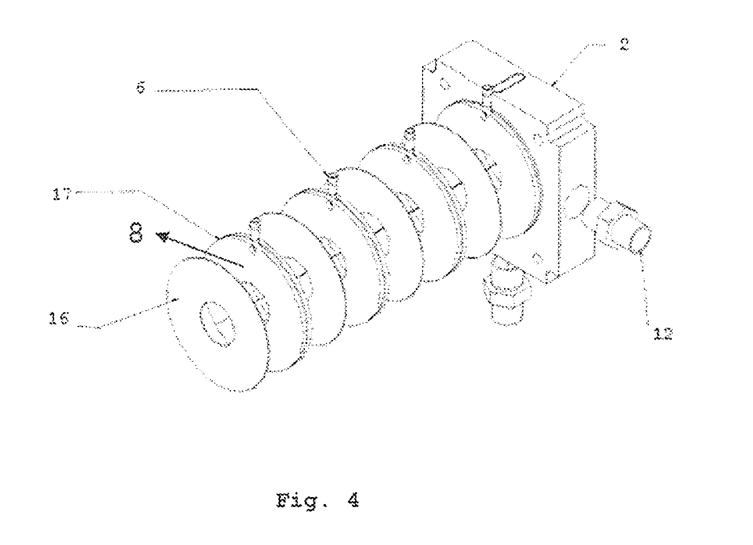
FIG. 4 is an exploded, schematic view of parts of the antenna unit according to embodiments of the present invention; wherein (2) is the antenna pack; (6) is the antenna electrical connector; (12) represents the outlet for the dissociated element; (16) represents dielectric mirrors; and (17) the assembled antenna.
Figure 5:
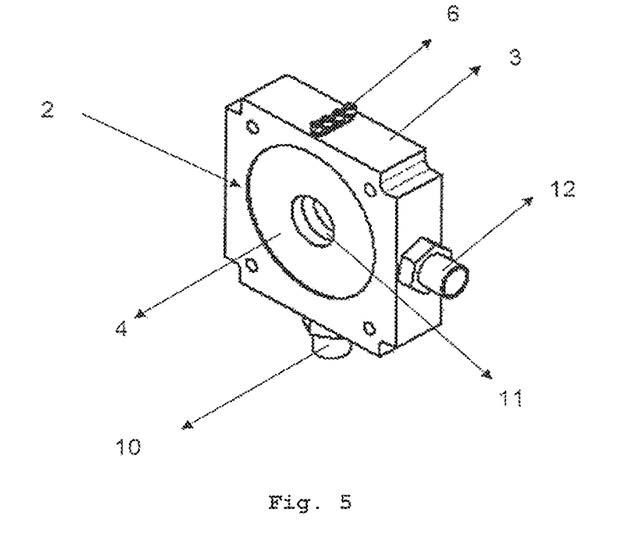
FIG. 5 is a schematic view of a concentric antenna pack with two outlets (10) and (12) wherein: (2) is the antenna support; (3) is the cover, containing the assembled antennas; (4) is the antenna plate; (6) are the antenna electrical connectors; and (11) is the circular space inlet for the substance to be dissociated.

The concentric antenna (see FIG. 4) comprises two conductive elements or plates (7, 8 in FIG. 2), in between which a Z-balanced impedance coil (9) made of a conductive material $\chi$ is placed, where $\chi$ represents the conductivity with $\eta$ number of windings of gauge $\phi$, so that when the relation between the material of said plates (7, 8) and the coils, the number of windings, the wire diameter and the wave function are maintained, an active antenna for dissociating compounds into their constituent elements is created.

The materials used in both coils and plates are those denoted as metal conductors where the conduction is an electronic conduction, i.e. the charge carriers are free electrons. Metal and alloys belongs to this group. Electrical conductivity is a property linked to the electrical current which can flow through a material being subjected to an electrical field, also and depending on the use of either a coil (9) or a plate (7, 8), it will be an indispensable requirement that the material of the plate (7, 8) also belongs to the group of magnetic materials, that is: a material is a magnetic material when its atoms or ions behave as if they were small magnets interacting between each other. "This behavior originates from the motion of electrons inside atoms, because the entire electrical current produces a magnetic field". In such cases, it is said that atoms have a magnetic momentum different from zero, characterized by its magnitude and the direction it is oriented. Plates that have been tested are made from the following materials: commercial ferric metals, steel, stainless steel, iron; in the case of coils the following materials have been tested: brass, aluminum, copper. In both cases (plate or coil), both had coatings of: silver, gold, tin, lead, zinc, magnesium, as well as alloys thereof.

ASSEMBLY EXAMPLES

Figure 7:
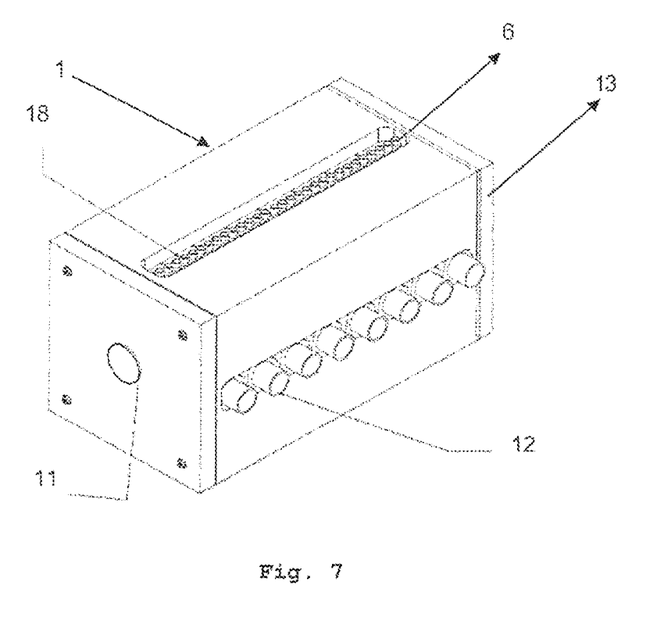
FIG. 7 is a schematic view of the dissociator according to embodiments of the present invention; wherein: (1) is the dissociator device; (6) are the antenna electrical connectors (which are connected to the signal generator); (11) is the circular space inlet for the substance to be dissociated; (12) is the outlet of the dissociated elements; (13) is the plastic cap; and (18) is the signal inlet from the generator.

A "magnetic resonance-based molecular dissociator (MRMD)" (1) was assembled comprising four antennas (FIG. 1), each one built as follows:

Two stainless steel plates (7, 8) type X3CrNb17 according to the European Standard (EN 10088), gauge 22, circular in shape and having a diameter of 15 cm, were made, with two bores, one of 0.625 cm on the upper portion thereof with a distance of 0.625 from the edge; in the center of the larger radius a bore was made, having a diameter of 2.5 cm; a washer (14), made of gauge 20 stainless steel sheet, with a radius of 3.5 cm and a central bore of 2.5 cm was welded thereto, and to which another plate was welded, forming a spool (see FIG. 7); in the spool bore at the joint between the washer and the two plates a thread was made, such that it would function as a nut for joining together other spools made in the same manner as above through the conducting conduit (see FIG. 8).

A coil (9) was made between plates (7, 8) with Nacobre brand wires type SOLDANELM. R. NYLON 130° C. and wire gauge 52. Said coil was made by placing a cable terminal in the hole with a terminal (6) on the upper portion of one of the plates and rotating the spool on a bench vise, until reaching the upper portion by covering the entire spool, leaving the other cable end in the adjacent plate hole; a pair of connectors were placed on both ends for conduction of electric current. Antennas are coated on the inside and outside creating a space where dissociated elements move and flow through de outlet cavity.

The four antennas were joined together with a tube (FIG. 8), by placing between them a 0.007-cm-thick circular rubber insulator, thus creating a space therein and placing a mirror (16) between the insulators.

The tube (FIG. 6) was made as follows: a copper mesh and a flexible iron mesh were selected, and a circular cylinder, 12.5 cm long and 2.5 cm wide, was formed by using as a mold a circular cylinder of 20 cm long and 2.5 cm in diameter having a thread, then wrapping the mesh around said mold; thereafter the entire mesh surface was covered with carbon fiber so as to provide it with rigidity, and then a wire was wrapped around said fiber conferring it a threaded shape, then it was heated at 300° C. for 90 minutes to provide rigidity.

Figure 9:
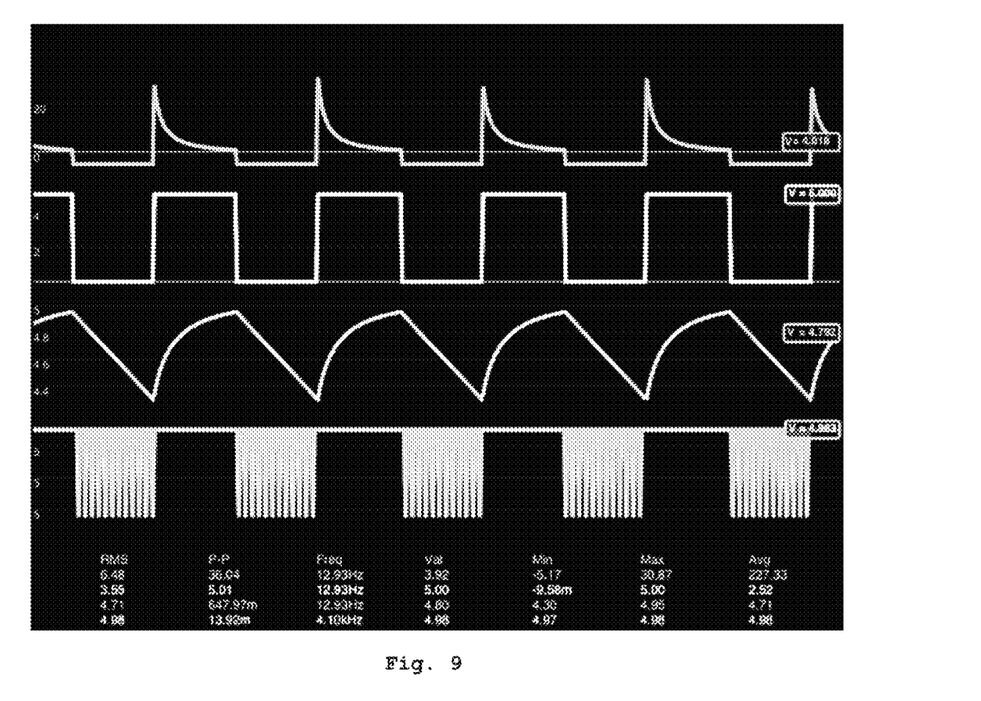
FIG. 9 is an image generated by the oscilloscope showing wave functions and frequencies used in the Signal Generator, in order to dissociate the elements contained in the Descriptive Examples of the invention. The wave function representation introduced in the antenna coil of the dissociator is shown in FIG. 9, wherein maximum voltage of 5.0 volts and frequency from 12.93 Hertz to 4.10 Kilohertz are clearly noted, said frequencies are very low and used for energizing or breaking molecules.

The antennas were attached to the tube and introduced in a casing (2) made of a 15×30×2.5 cm plastic cube, to which a 15-cm through hole was made in the center thereof, and a groove was formed on one side so as to allow projecting the coil (6) terminals, and a bore of 1.25 cm was made on the sides thereof towards the washer edge but not reaching the tube, so as to perforate all the antennas (see FIG. 9). Said perforation was then threaded and a PVC nipple (11, 12) with 1.25-cm Teflon tape around its thread and covering said perforation, was screwed therein; then the whole was sealed with COMEX silicone in order to ensure that everything would flow into the corresponding cavities; then the cube was ground flush with the spools on each end of the dissociator.

Once the primary dissociator was developed, 7 additional devices (dissociators) were manufactured, and then placed into a plastic container, with the necessary cavities allowing for the projection of connectors, nipples and the fluid conduction tube. Finally, plastic caps (13) were made from the same material containing the antennas, and then sealed and fixed with stainless steel screws of an unknown brand, in order to avoid corrosion.

Once the dissociator was completed, a 6-channel wave signal generator, HIGHLANDER TECHNOLOGY, was connected thereto, and this in turn was connected to a signal delayer, of the same brand, then different fluids flowed through the central tube and a plug was placed on the other end of the tube ("depending, as the case may be, on the fluid type"), and different elements and materials were obtained from the lateral and bottom outlets.

APPLICATION EXAMPLES

For the case of tap water:

Lab-type rubber tubings of unknown brand were placed, where test tubes were placed with cork plugs, water was filled into the test tubes and then placed upside down in a 23×30 cm container, which then was filled with water until covering the mouth of said test tubes; each tube was sealed with a rubber stopper having two holes to which two glass tubings were placed, where one tubing was connected to one of the dissociator's rubber tubings on the outlets (10, 12), and the other tubing was left unconnected; when wave functions (FIG. 9) were induced and tap water was circulated, different materials were obtained inside each tube: oxygen in one and hydrogen in the other, which was determined because gas production was twice as high as compared to the other; and in the last one: chlorine. The latter was characterized by its odor and resultant mixture of solid materials, which are considered to be salts not yet identified.

As can be noted from the example, the elements to be dissociated within the dissociator are within a fluid combined with other organic and inorganic elements. Fluid is flowed through the center of the antenna (11). Dissociators can be single or multiple dissociators, depending on the number of antennas linked together.

As the number of antenna units increases (FIG. 1), the volume of the compound, or multiple elements, to be dissociated can increase simultaneously, applying a single- or multi-frequency spectrum, respectively.

As can be appreciated, each antenna is spaced apart by an insulator or dielectric at a distance θ where the dissociated element will be obtained by inducing a wave function to the coil, thus creating a resonance frequency corresponding to each element, said elements exiting the outlets (10, 12), and the remaining elements will be output as residue on the rear portion.

On each antenna device a resonance frequency or various resonance frequencies exist, as long as a number of coils exist; for this reason there are outlets for dissociated elements on the sides of the dissociator, and one inlet and one outlet on the rear portion of the dissociator for connection to a new device, or it may be provided with a conduit cap.

All windings increase their number of turns from the center of the antenna and outwardly; thus, the dissociation step occurs by energizing the incoming fluid all the way to the end of the path, where bond rupture occurs. Winding positions yield distinctive electromagnetic radiation patterns.

Figure 10:
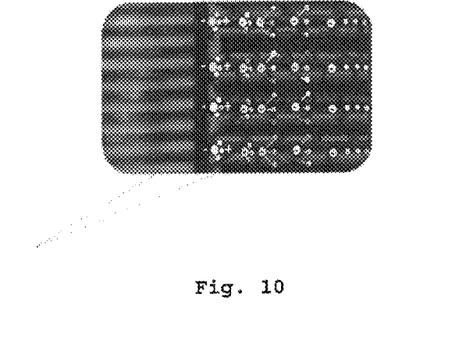
FIG. 10 is a graphic representation of how a molecule passes from a polarized state to a dissociated state; representing the steps that occur from the introduction of the element to be dissociated in the invention until the dissociated elements exit the outlets (10, 12).

Regarding FIG. 10, there is shown how a molecule passes from a polarization state into a dissociation state.

To the knowledge of the inventor of embodiments of the present invention, unlike the present invention there is no device capable to dissociate molecules into their constituent elements without using electrodes immersed in the media to be dissociated.

For the case of saltpeter water:

This kind of water is called as such because it is a viscous liquid obtained from deep wells, wherein water is combined with salts, minerals, rocks and, in some cases oil (crude oil); the objective is to separate water, rocks, and leave minerals and oil in the same mixture, which undergoes separation in industrial refining processes. Currently, the process is carried out using floating ceiling tanks and adding chemical substances, thus allowing for the flotation of water and thus carrying out said separation.

In our example, water containing crude oil, extracted from a well from Petroleos Mexicanos, was used.

The prototype employed was initially the same as in the case of tap water, but a rotary drum was added for separation of rocks with a thickness greater than 0.01 mm at the dissociator inlet.

Lab-type rubber tubings of unknown brand were placed, where test tubes were placed with cork plugs; water was filled into the test tubes and then placed upside down in a 23×30 cm container, which then was filled with water until covering the mouth of said test tubes. Each tube was sealed with a rubber stopper having two holes to which two glass tubings were placed: to one of said tubings one of the dissociator's rubber tubings was connected to the outlet (10, 12) to each tube with rubber tubings, and the other tubing was left unconnected. When wave functions were induced and saltpeter water was circulated, different materials were obtained inside each tube: oxygen in one and hydrogen in the other, which was determined because gas production was twice as high as compared to the other. The remaining material was placed in where the oil was poured with mineral salts in the form of sand.

It is worth mentioning that the above mentioned descriptive examples, are included in a descriptive but not limiting manner, because the present invention is capable of practically dissociating any fluid into its elements.

The invention claimed is:

1. A resonance-based molecular dissociator comprising:
a series of antenna units configured to provide continuous wave functions that produce an electromagnetic field on each antenna unit in the series of antenna units, the continuous wave function having a frequency and a time variation, through which a fluid comprising an element to be dissociated passes, wherein each said antenna unit of the series of antenna units comprises:
at least two antenna plates separated by at least one washer;
an antenna electrical connector;
a balanced impedance coil;
a sealing insulator;
a multi-section solenoid;
an antenna pack;
at least two outlets for the element dissociated from the fluid to exit from the resonance-based dissociator;
a dielectric; and
a circular space inlet for the fluid to be dissociated;
a fluid distribution conduit within the resonance-based molecular dissociator;
a plastic container with a plastic cap for containing the series of antenna units; and
a signal generator connected to the antenna electrical connector of each antenna unit in the series of antenna units.

2. The resonance-based dissociator according to claim 1, wherein said series of antenna units generate a spectral pattern of radiation having a resonance frequency.

3. The resonance-based dissociator according to claim 1, wherein each antenna unit of the series of antenna units further comprises a body or support having a plurality of concentric antennas placed therein and a hollow circular space in a center of the body or support where the fluid distribution conduit is placed, allowing circulation of the fluid to be treated through said fluid distribution conduit.

4. The resonance-based dissociator according to claim 3, wherein the at least two antenna plates are joined together and have two bores on an upper portion of the at least two antenna plates at a distance from an edge;
a bore in a center of the at least two antenna plates having a diameter of a same size as a diameter of the fluid distribution conduit;
the at least one washer separating the at least two antenna plates has a central bore and the at least one washer is welded to the hollow circular space in the center of the body or support forming a spool at a joint between the at least one washer and the at least two plates; and
within the spool, at the joint where the at least one washer joins with the at least two antenna plates, a thread is made.

5. The resonance-based dissociator according to claim 3, wherein the plurality of concentric antennas each comprise two conductive elements or plates;
the balanced impedance coil is made of a conductive material;
an active antenna is created from the balanced impedance coil having a number of windings, a wire diameter, and the continuous wave function; and
the active antenna dissociates the element from the fluid.

6. The resonance-based dissociator according to claim 1, wherein the at least two outlets of each antenna unit are lateral outlets through which the element dissociated from the fluid exits from the antenna unit and the continuous wave functions are provided at the antenna electrical connectors.

7. The resonance-based dissociator according to claim 1, wherein said resonance-based dissociator is assembled with an increased number of antenna units until achieving a pattern suitable for an amount of the element to be dissociated from the fluid at a smallest time interval of fluid circulation.

8. The resonance-based dissociator according to claim 1, wherein the at least two antenna plates are comprised of conductive plates; and
between the conductive plates and around the washer, the balanced impedance coil is created with windings starting and ending on the antenna electrical connectors connecting the conductive plates to the signal generator.

9. The resonance-based dissociator according to claim 1, wherein the fluid distribution conduit through which the fluid passes has a shape of a circular cylinder comprising a copper mesh, a flexible iron mesh with a thread, carbon fiber covering the copper mesh and flexible iron mesh and a wire wrapped around the carbon fiber conferring upon the carbon fiber a threaded shape.

10. The resonance-based dissociator according to claim 1, wherein materials used in both the balanced impedance coil and the at least two antenna plates are metal conductors or metal alloy conductors that perform electronic conduction.

11. The resonance-based dissociator according to claim 1, wherein the at least two antenna plates are constructed out of a magnetic material selected from the group consisting of commercial ferric metals, steel, stainless steel, and iron.

12. The resonance-based dissociator according to claim 1, wherein said resonance-based dissociator is connected to an at least 6-channel wave signal generator, and said at least 6-channel wave signal generator is connected to a signal delayer.

* * * * *